United States Patent [19]

Ozmeral et al.

[11] Patent Number: 4,474,912

[45] Date of Patent: Oct. 2, 1984

[54] STABLE WATER-IN-OIL EMULSIONS CONTAINING POLYOXYALKYLENE BLOCK COPOLYMERS

[75] Inventors: Ahmet C. Ozmeral, Baton Rouge, La.; Irving R. Schmolka, Grosse Ile, Mich.

[73] Assignee: BASF Wyandotte Corporation, Wyandotte, Mich.

[21] Appl. No.: 527,102

[22] Filed: Aug. 29, 1983

[51] Int. Cl.³ .................. A61K 47/00; A01N 9/04
[52] U.S. Cl. .................. 523/337; 424/168; 424/170; 424/199; 523/102; 523/105; 524/491
[58] Field of Search ............ 424/168, 170, 199; 524/491; 523/102, 105, 337

[56] References Cited

U.S. PATENT DOCUMENTS

| | | | |
|---|---|---|---|
| 2,828,345 | 3/1958 | Spriggs | 252/311 |
| 3,062,721 | 11/1962 | Grate | 424/199 |
| 3,776,857 | 12/1973 | Lindner | 424/168 |
| 3,846,546 | 11/1974 | Lachampt et al. | 424/170 |
| 4,022,736 | 5/1977 | Schmitt | 523/337 |
| 4,115,314 | 9/1978 | Oppenläender et al. | 424/170 |
| 4,183,821 | 1/1980 | Langdon et al. | 252/331 |
| 4,357,353 | 11/1982 | Strauss et al. | 424/199 |
| 4,370,319 | 1/1983 | Chapin et al. | 424/170 |
| 4,384,974 | 5/1983 | Guthauser | 424/170 |

*Primary Examiner*—Ronald W. Griffin
*Attorney, Agent, or Firm*—Bernhard R. Swick

[57] ABSTRACT

The instant invention relates to water-in-oil emulsions which are non-irritating to the skin, low in toxicity, colorless and easy to wash off, which contain as the emulsifying agent a polyoxyalkylene compound of the formula:

$$Y(A)_m-(B)_n H$$

wherein Y is the residue formed by the removal of one atom of active hydrogen from a suitable initiator, A is a hydrophobic, heteric mixture of an oxytetramethylene radical, derived from tetramethylene oxide and a vicinal alkylene oxide radical derived from propylene oxide; B is primarily $C_2H_4O$; m is an integer such that the total molecular weight of the hydrophobe is about 500 to 2000 and n is an integer such that B is about 20 to 50 percent of the total weight of the compound.

12 Claims, No Drawings

STABLE WATER-IN-OIL EMULSIONS CONTAINING POLYOXYALKYLENE BLOCK COPOLYMERS

BACKGROUND OF THE INVENTION

Field of the Invention

This invention relates to water-in-oil emulsions and more particularly stable water-in-oil emulsions containing polyoxyalkylene block copolymers.

Water-in-oil emulsions are useful in the preparation of cosmetics and pharmaceuticals, insecticides, etc. However, in the past it was generally believed that in order to create a stable water-in-oil emulsion it was necessary to employ, as an emulsifier, material that was soluble in the oil and insoluble in water. Water-in-oil emulsions employing such emulsifiers have the disadvantage that they are difficult to wash off the surface to which they have been applied. Accordingly, it is the purpose of the instant invention to provide water-in-oil emulsions for uses such as applications to the skin wherein the emulsion can be easily washed off. It is also a purpose of the invention to provide a stable water-in-oil emulsion of such type which is also non-irritating to the skin, non-toxic and colorless. The latter is desirable since if a color is desired it will be easy to obtain the desired color by use of a simple dye or other coloring material without being affected by the color of the water-in-oil emulsion itself.

U.S. Pat. No. 4,183,821 discloses crude oil demulsifier compounds which are block copolymers of tetrahydrofuran, propylene oxide and ethylene oxide.

U.S. Pat. No. 2,828,345 discloses surface active hydroxypolyoxyethylene diethers of polyoxybutylene glycols and that these compounds have emulsifying power in that they form stable oil-in-water emulsions.

An article by Kuwamura et al, Journal of the American Oil Chemists' Society, 48, pp. 29–34 (1971), entitled "Surface-active Block Copolymers: 1. The Preparation and Some Surface-active Properties of Block Copolymers of Tetrahydrofuran and Ethylene Oxide," discloses such surface-active copolymers.

SUMMARY OF THE INVENTION

The instant invention relates to water-in-oil emulsions which are non-irritating to the skin, low in toxicity, colorless and easy to wash off, which contain as the emulsifying agent a polyoxyalkylene compound of the formula:

$$Y(A)_m—(B)_nH$$

wherein Y is the residue formed by the removal of one atom of active hydrogen from a suitable initiator, A is a hydrophobic, heteric mixture of an oxytetramethylene radical, derived from tetramethylene oxide and a vicinal alkylene oxide radical derived from propylene oxide; B is primarily $C_2H_4O$; m is an integer such that the total molecular weight of the hydrophobe is about 500 to 2000 and n is an integer such that B is about 20 to 50 percent of the total weight of the compound.

DETAILED DESCRIPTION OF THE INVENTION

The nonionic emulsifying agent may be more specifically described as a polyoxyalkylene compound of the formula:

$$Y(A)_m—(B)_nH$$

wherein Y is the residue of an organic compound containing therein a single hydrogen atom capable of reacting with an alkylene oxide. Examples of Y include the residue from compounds such as the monofunctional alcohols, e.g., methanol, butanol, etc.; aliphatic acids such as formic acid, acetic acid, butanoic acid; secondary amines such as diethylamine, ethylbutylamine, etc.; and substituted amides such as methylacetamide, aliphatic mercaptans such as methyl and butyl mercaptan, etc.; said initiator preferably being n-butanol. A is a hydrophobic, heteric mixture of an oxytetramethylene radical, derived from tetramethylene oxide and a vicinal alkylene oxide radical derived from propylene oxide, said A being derived from the reaction of said oxides in the molar ratio of tetramethylene oxide: vicinal alkylene oxide of 3:1 to about 1:3; B is primarily $C_2H_4O$; n is an integer such that B is about 30 to 50 percent of the total weight of the compound and m is an integer such that the total molecular weight of the hydrophobe is about 500 to 2000, preferably about 750 to 1500.

The hydrophobe A may optionally but advantageously contain small amounts up to 30 percent by weight of oxyethylene and/or oxybutylene groups while the hydrophile B may also optionally but advantageously contain oxypropylene and oxybutylene groups in amount up to 30 weight percent of the total hydrophilic portion of the molecule. As used herein, reference to the hydrophobic groups, or group A, is considered to include such optional groups even though not specifically mentioned and, similarly, reference to the hydrophilic groups or group B is considered to possibly include such oxypropylene or oxybutylene groups. The preparation of the compounds of the type set forth in the above formula is described in more detail in U.S. Pat. No. 4,183,821.

The oil component of this emulsion is mineral oil. By the expression "mineral oil" is meant a clear, colorless, nearly odorless and tasteless liquid obtained from the distillation of petroleum. It is also called white oil, white mineral oil, liquid petrolatum, liquid paraffin or white paraffin oil. Mineral oil is a highly refined oily liquid which is commercially available as a technical grade, as a NF (national formulary) grade and as a USP grade. The viscosity of mineral oil generally lies between about 38 and 385 SUS at 100° F. Mineral oil is usually free of aromatics and unsaturated compounds. Further information on commercially available mineral oil is found in the *Chemical Week* 1983 Buyer's Guide, issued October 1982, page 442, which is hereby incorporated by reference. Any mineral oil described therein is suitable for the instant invention.

The water/oil ratio may range from about 15:85 to 45:55 by weight. The amount of the polyoxyalkylene compound present in the water-in-oil emulsion may range from about 1 to 15 percent of the total weight of the emulsion composition.

The water-in-oil emulsions of the instant invention have many potential uses in cosmetic, pharmceutical and insecticide applications. They are compatible with most of the known primary treatment agents used in cosmetic, pharmaceutical and insecticide formulations. At least one primary treatment agent may be included in the emulsion in amount of about 1 to 10 percent, and preferably about 2 to 5 percent, of the total weight of the composition. For example, the emulsions of the invention may be compounded with deodorants and antiperspirants. Simple deodorants such as oxyquinoline salts and zinc oxide; astringents such as aluminum chlorohydrate; antiseptics such as diisobutylphenoxyethoxyethyldimethyl benzyl ammonium chloride and hexachlorodihydroxydiphenylmethane; and pesticides such as boric acid; hexachlorophene and N,N-diethyltoluamide may be compounded with the water-in-oil emulsions of this invention. These emulsions may be used in shampoos, skin creams and for hair products. Also, the emulsions of this invention may contain hydrogen peroxide; materials for treating planters warts, such as cantharadin, ingredients for treating athlete's foot such as undecylenic acid, as well as various anti-psoriasis drugs, vitamins, and other drugs.

The emulsions of the instant invention may also include at least one adjuvant. These could include proteins, amino acids, electrolytes and other ingredients normally found in external body fluids. Humectants such as propylene glycol or glycerine may also be included. Further adjuvants could include silicone oils. Also, other ingredients which impart further desired qualities to the skin may be incorporated in the compositions according to this invention, e.g., skin fresheners, emollients or the like such as lanolin or its derivatives, lecithin, higher alcohols, dipelargonate ethers or esters, coconut oil and other fatty esters and mixtures thereof may generally be used in minor proportions. Furthermore, coloring materials such as dyes and perfumes may be used as desired. The amount of adjuvants would range from about 1 to 25 percent and preferably from about 3 to 15 percent of the total weight of the emulsion.

The following examples are included to further illustrate the present invention. As used throughout this application, unless otherwise stated, all parts and percentages are by weight.

EXAMPLES 1-15

The emulsions of these examples were prepared by dissolving the emulsifier in distilled water and placing this solution in a wide-mouth steel container with light mineral oil and emulsifying the mixture in an electric mixer at high speed (800 rpm) for three minutes. The mineral oil was a commercial product sold by Penneco Division of Pennzoil, Butler, Pa., under the trademark Drakeol #5. The emulsifier was a polyoxyalkylene compound according to the formula set forth above having an n-butanol initiator and where the tetramethylene oxide:propylene oxide molar ratio in A of the formula is 1:1, m is an integer such that the total molecular weight of A is about 1000, and n is an integer such that B is about 40 percent of the total weight of the compound. The weight ratio of water-to-mineral oil and the amount of emulsifier in percent of the total emulsion composition for these examples is shown in Table I below.

Fifty milliliters of each mixture was transferred to a ¾ by 12½ inch tube and allowed to stand for 24 hours at ambient temperature. Those samples that did not separate after 24 hours are indicated in Table I by a "+" and those which did separate during the 24-hour period are indicated by a "—".

At the conclusion of the 24-hour tests, each mixture which did not separate was subjected to freeze-thaw cycles. This is an accelerated stability test widely used in the cosmetic industry for determining the long-term stability of emulsions. This comprises placing the emulsion-containing tubes in a refrigerator for 8 to 10 hours at 40° F., then placing in an oven for 8 to 10 hours at 120° F. and repeating these steps for another four cycles. In the appropriate column of Table I below is indicated the number of freeze-thaw cycles completed without separation.

TABLE I

| Example No. | Water/ Mineral Oil Ratio | % Emulsifier | 24-Hour Test | Freeze-Thaw Cycles Completed Without Separation |
|---|---|---|---|---|
| 1 | 20/80 | 10 | — | — |
| 2 | 20/80 | 5 | + | 5 |
| 3 | 20/80 | 1 | + | 5 |
| 4 | 25/75 | 10 | + | 5 |
| 5 | 25/75 | 5 | + | 5 |
| 6 | 25/75 | 1 | + | 5 |
| 7 | 30/70 | 10 | + | 5 |
| 8 | 30/70 | 5 | + | 5 |
| 9 | 30/70 | 1 | + | 5 |
| 10 | 35/65 | 10 | + | 5 |
| 11 | 35/65 | 5 | + | 2 |
| 12 | 35/65 | 1 | — | — |
| 13 | 40/60 | 10 | + | 2 |
| 14 | 40/60 | 5 | + | 1 |
| 15 | 40/60 | 1 | — | — |

EXAMPLES 16-21

Six water and mineral oil emulsions were prepared as described for Examples 1-15 whereby direct comparisons were made at three water/oil ratios between the emulsifier as described in Examples 1-15 and a commercial emulsifier indicated herein as Commercial #1 using one part by weight of emulsifier per 100 parts of the total composition. These were allowed to stand for 24 hours and those that did not separate were subjected to five freeze-thaw cycles as described in Examples 1-15. The results of these tests are shown in Table II below. The commercial emulsifier was a modified alkanolamide.

TABLE II

| Example No. | Emulsifier | Water/ Mineral Oil Ratio | 24-Hour Test | Freeze-Thaw Cycles Completed Without Separation |
|---|---|---|---|---|
| 16 | Invention | 20/80 | + | 5 |
| 17 | Commercial #1 | 20/80 | — | — |
| 18 | Invention | 25/75 | + | 5 |
| 19 | Commercial #1 | 25/75 | — | — |
| 20 | Invention | 30/70 | + | 5 |
| 21 | Commercial #1 | 30/70 | — | — |

EXAMPLES 22-27

Direct comparisons were made between the emulsifier described in Examples 1-15 according the the instant invention and three different commercial emulsifiers, indicated herein as commercial #2, #3, etc., when employed in three different cosmetic formulations. Commercial #2, sorbitan sesquioleate, is a non-water soluble emulsifier. Commercial #3 is diethyl aminoethyl stearate and Commercial #4 is polyglyceryl-4-oleate. These compositions were tested as described in Examples 1-15 and the results shown in Table III below.

TABLE III

| Example No. | Formulation No. | Type of Emulsifier | 24-Hour Test | Freeze-Thaw Cycles Completed |
|---|---|---|---|---|
| 22 | 1 | Invention | + | 5 |
| 23 | 1 | Commercial #2 | + | 5 |
| 24 | 2 | Invention | + | 3 |
| 25 | 2 | Commercial #3 | + | 0 |
| 26 | 3 | Invention | + | 3 |
| 27 | 3 | Commercial #4 | + | 0 |

In the cosmetic formulations it can be seen that the emulsifier of the instant invention was as good as or superior in the emulsion stability tests when compared to the commercial emulsifiers #2 to #4. While emulsifier #2 appears to be equal in emulsion stability to that of the instant invention when employed in cosmetic formulation #1, emulsifier #2 is not water soluble. Therefore, it would be difficult to wash off whereas the instant emulsifier is water soluble and the cosmetic formulation can be easily washed off. According to prior knowledge, it was generally believed that an emulsifier for these purposes would have to be water insoluble.

Formulations #1 to #3 are as follows:

| Formulation #1 | |
|---|---|
| Mineral Oil | 50.0% |
| Beeswax | 10.0 |
| Emulsifier | 1.0 |
| Lanolin | 3.1 |
| Borax | 0.7 |
| Water | 35.2 |
| | 100.0% |

| Formulation #2 | |
|---|---|
| Mineral Oil | 44.0% |
| Petrolatum | 10.0 |
| Beeswax | 5.0 |
| Emulsifier | 3.0 |
| Lanolin | 1.0 |
| Diisopropyl adipate | 6.0 |
| Water | 30.1 |
| Borax | 0.4 |
| MgSO$_4$ | 0.5 |
| | 100.0% |

| Formulation #3 | |
|---|---|
| Mineral Oil | 50.0% |
| Petrolatum | 10.0 |
| White Beeswax | 5.0 |
| Emulsifier | 3.0 |
| Lanolin | 1.0 |
| Diisopropyl adipate | 6.0 |
| Borax | 0.4 |
| MgSO | 0.5 |
| Water | 24.1 |
| | 100.0% |

EXAMPLE 28

Water-in-oil emulsions using water-to-oil ratios of 20:80, 25:75 and 30:70 water-in-mineral oil were prepared without using any emulsifier. The water-in-oil layers separated within minutes.

The embodiments of this invention in which an exclusive property or privilege is claimed are defined as follows:

1. A water-in-oil emulsion comprising water, mineral oil, and an emulsifying amount of a polyoxyalkylene compound having the formula $$Y(A)_m\text{—}(B)_n H$$

wherein Y is the residue formed by the removal of one atom of active hydrogen from a monofunctional initiator, A is a hydrophobic, heteric mixture of an oxytetramethylene radical, derived from tetramethylene oxide and a vicinal alkylene oxide radical derived from propylene oxide, said A being derived from the reaction of said oxides in the molar ratio of tetramethylene oxide:-vicinal alkylene oxide of 3:1 to 1:3; B is $C_2H_4O$; n is an integer such that B is about 30 to 50 percent of the total weight of the compound and m is an integer such that the total molecular weight of the hydrophobe is about 500 to 2000.

2. The water-in-oil emulsion of claim 1 wherein the value of m is such that the total molecular weight of the hydrophobe is about 750 to 1500.

3. The water-in-oil emulsion of claim 1 wherein the ratio of water to oil is from about 15:85 to 45:55 and the amount of said emulsifier is from about 1 to 15 percent of the total weight of the emulsion composition.

4. The oil-in-water emulsion of claim 3 including at least one primary treatment agent in amount of about 1 to 10 percent of the total weight of the composition.

5. The water-in-oil emulsion of claim 4 including at least one adjuvant in amount of about 1 to 25 percent of the total weight of the composition.

6. The water-in-oil emulsion of claim 5 wherein the primary treatment agent is selected from the group consisting of: deodorants, antiperspirants, astringents, antiseptics, pesticides, materials for treating planters warts and athelete's foot, antipsoriasis drugs and vitamins and the adjuvant is selected from the group consisting of: proteins, amino acids, electrolytes, humectants, silicone oils, skin fresheners, dipelargonate ethers and esters, dyes and perfumes.

7. A method of producing stable water-in-mineral oil emulsions comprising adding thereto an emulsifying amount of a polyoxyalkylene compound having the formula $$Y(A)_m\text{—}(B)_n H$$

wherein Y is the residue formed by the removal of one atom of active hydrogen from a monofunctional initiator, A is a hydrophobic, heteric mixture of an oxytetramethylene radical, derived from tetramethylene oxide and vicinal alkylene oxide radical derived from propylene oxide, said A being derived from the reaction of said oxides in the molar ratio of tetramethylene oxide:-vicinal alkylene oxide of 3:1 to 1:3; B is $C_2H_4O$; n is an integer such that the total weight of said B is about 30 to 50 percent by weight of the total oxyalkylene residue weight of the compound and m is an integer such that the total molecular weight of the hydrophobe is about 500 to 2000.

8. The method of claim 7 wherein the value of m is such that the total molecular weight of the hydrophobe is about 750 to 1500.

9. The method of claim 7 wherein the ratio of water to oil is from 15:85 to 45:55 and the amount of said emulsifier is from about 1 to 15 percent of the total weight of the composition.

10. The method of claim 9 wherein said emulsion includes at least one primary treatment agent in amount of about 1 to 10 percent of the total weight of the composition.

11. The method of claim 10 wherein said emulsion includes at least one adjuvant in amount of about 1 to 25 percent of the total weight of the composition.

12. The method of claim 11 wherein the primary treatment agent is selected from the group consisting of: deodorants, antiperspirants, astringents, antiseptics, pesticides, materials for treating planters warts and athlete's foot, antipsoriasis drugs and vitamins and the adjuvant is selected from the group consisting of: proteins, amino acids, electrolytes, humectants, silicone oils, skin fresheners, dipelargonate ethers and esters, dyes and perfumes.

* * * * *